US010543276B2

(12) United States Patent
Forrester et al.

(10) Patent No.: US 10,543,276 B2
(45) **Date of Patent: *Jan. 28, 2020**

(54) TOPICAL COMPOSITIONS

(71) Applicant: Marlinz Pharma, LLC, Houston, TX (US)

(72) Inventors: Perry Forrester, Houston, TX (US); Joshua Scott, Houston, TX (US)

(73) Assignee: Marlinz Pharma, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/225,980

(22) Filed: Dec. 19, 2018

(65) Prior Publication Data

US 2019/0201531 A1 Jul. 4, 2019

Related U.S. Application Data

(63) Continuation-in-part of application No. 15/671,719, filed on Aug. 8, 2017, now Pat. No. 10,251,858.

(60) Provisional application No. 62/372,132, filed on Aug. 8, 2016.

(51) Int. Cl.

| | |
|---|---|
| ***A61K 47/22*** | (2006.01) |
| ***A61K 47/12*** | (2006.01) |
| ***A61K 9/00*** | (2006.01) |
| ***A61K 47/18*** | (2017.01) |
| ***A61K 47/14*** | (2017.01) |
| ***A61K 47/10*** | (2017.01) |

(52) U.S. Cl.

CPC ............ *A61K 47/22* (2013.01); *A61K 9/0014* (2013.01); *A61K 47/10* (2013.01); *A61K 47/12* (2013.01); *A61K 47/14* (2013.01); *A61K 47/18* (2013.01)

(58) Field of Classification Search

None

See application file for complete search history.

(56) References Cited

U.S. PATENT DOCUMENTS

| | | | |
|---|---|---|---|
| 4,810,498 | A | 3/1989 | DiMeglio |
| 5,519,059 | A | 5/1996 | Sawaya |
| 5,525,635 | A | 6/1996 | Moberg |
| 6,391,879 | B1 | 5/2002 | Reeves |
| 7,074,392 | B1 | 7/2006 | Friedman |
| 7,374,772 | B2 | 5/2008 | Bommarito |
| 8,333,981 | B2 | 12/2012 | Trimble |
| 8,952,070 | B2 | 2/2015 | Lindahl |
| 8,987,330 | B2 | 3/2015 | Karlsson |
| 9,561,279 | B2 | 2/2017 | Lindahl |
| 9,782,372 | B2 | 10/2017 | Karlsson |
| 2011/0207765 | A1 | 8/2011 | Van Den Bussche |
| 2012/0010227 | A1 | 1/2012 | Lusiana |
| 2012/0129942 | A1 | 5/2012 | Lindahl |
| 2015/0306052 | A1 | 10/2015 | Karlsson |
| 2017/0258917 | A1 | 9/2017 | Lindahl |

OTHER PUBLICATIONS

Crawford, et al., Topical Treatments for Fungal Infections of the Skin and Nails of the Foot, The Cochrane Collaboration, 1999, Issue 3.

podiatrynetwork.com, Topical Treatment for Fungal Toenails, www.podiatrynetwork.com/document_disorders.cfm?id=313, accessed Jul. 14, 2016.

Faergemann, et al., Early and Visible Improvements after Application K101 in the Appearance of Nails . . . , J. of Cosmetics, 2011, 1 , 59-63.

*Primary Examiner* — Jessica Worsham

(74) *Attorney, Agent, or Firm* — Bushman Werner, P.C.

(57) ABSTRACT

A pharmaceutically active composition containing an effective amount of a pharmacologically active ingredient such as an antifungal and a carrier. The carrier comprises dimethyl isosorbide, undecylenic acid, a lower carboxylic acid other than undecylenic acid, a monohydric alcohol having from 2 to 4 carbon atoms, and urea.

20 Claims, 1 Drawing Sheet

TOPICAL COMPOSITIONS

CROSS REFERENCE TO RELATED APPLICATION

This application is a continuation-in-part of U.S. application Ser. No. 15/671,719 filed on Aug. 8, 2017, which in turn claims priority to U.S. 62/372,132, the disclosures of which are incorporated herein by reference for all purposes.

FIELD OF THE INVENTION

The present invention relates to topical compositions for skin tissue including nails and, in particular, to liquid carriers/vehicles for pharmacologically active components forming the topical coposition.

BACKGROUND OF THE INVENTION

Compositions for topical application to the skin, whether purely cosmetic, pharmaceutical, or mixtures thereof, heavily rely on the penetrating ability of the composition for maximum efficacy. For example, treatments of fungal infections of the toe nail, or toe nail discoloration due to other underlying factors, are largely dependent on the ability of the active agent, an antifungal to penetrate the skin surrounding the nail as well as the nail itself. In this regard nails are actually produced by living skin cells in the toe or finger.

Additionally certain ingredients used in cosmetic applications can hydrate, thin, and normalize the color of nails and skin. Rehydrating a fungal nail that is dehydrated and dried out can increase porosity of the cells in the nail matrix making it easier for penetration of agents needed to treat the nail, e.g., for fungus.

With particular respect, and by way of example only, for the treatment of nail disorders such onychomycosis or psoriasis affecting the nails, a widely used prescription antifungal is sold under the trademark Jublia®. The composition of the Jublia® antifungal composition, uses a vehicle in which the active ingredient is dissolved, which preferably comprises a linear or branched aliphatic lower alcohol, such as ethanol, methanol, propanol, or isopropanol. U.S. Pat. No. 10,05,444 ('444 patent), incorporated herein by reference for all purposes, covers the Jublia® antifungal composition. The '444 patent encompasses and is focused on the fact that the composition claimed therein meets a significant need for a pharmaceutical composition that provides for enhanced penetration of a pharmaceutical agent contained within the composition into, under, around, and through a nail into the nail bed. To accomplish enhanced penetration, and in addition to the lower alcohol, the composition of the '444 patent also relies on a surfactant to reduce surface tension and a volatile silicone to act as a wetting agent. In any event, the teachings of the '444 patent highlight the fact that penetration is quite important in successfully treating skin disorders, e.g., fungal infections, of the nails and surrounding tissue.

SUMMARY OF THE INVENTION

In one aspect, the present invention relates to an antifungal composition for application to the toe nail and adjoining tissue.

In another aspect, the present invention relates to a pharmaceutically active composition for the treatment of fungal infections on and surrounding the toe nail.

In still a further aspect, the present invention relates to a composition comprising a carrier and an effective amount of a pharmaceutically active antifungal component wherein the antifungal component is uniformly dispersible in a carrier.

In yet another aspect, the present invention relates to a carrier or vehicle for use in the topical application of dermatologically active ingredients.

In still another aspect, the present invention relates to a carrier for use in topical application of dermatologically active ingredients which exhibits good penetrating ability.

These and further features and advantages of the present invention will become apparent from the following detailed description, wherein reference is made to the figures in the accompanying drawings.

DETAILED DESCRIPTION OF PREFERRED EMBODIMENTS

Figure 1:
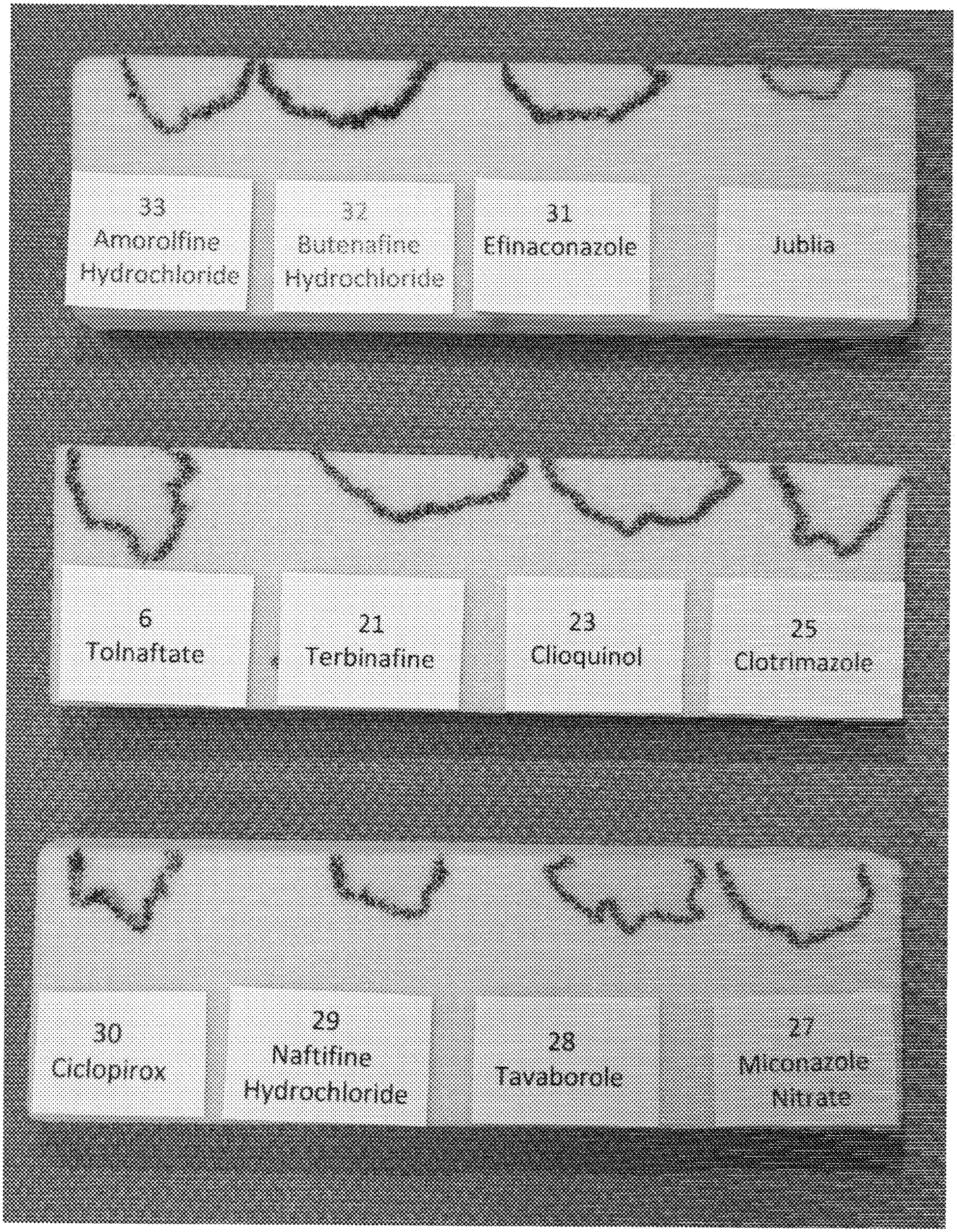
FIG. 1 shows the penetrating ability of the compositions of the present invention as compared to a widely used commercial prior art product.

As used herein, the terms "nail" or "nails" means one or more of the toe nails and/or finger nails of an animal, particularly humans.

Broadly, the present invention comprises a liquid carrier or vehicle for dermatologically active ingredients (DAIs), e.g., antifungals or cosmetic components, to form a dermatologically active composition (DAC). In its basic form, the liquid carrier or vehicle comprising the present invention contains dimethyl isosorbide, undecylenic acid, a carboxylic acid component other than undecylenic acid, a monohydric alcohol having from 2 to 4 carbon atoms, and a urea based component.

In general, the carrier will contain:

- from greater than 0 to about 40% by weight, preferably from greater than 0 to about 25% by weight, more preferably from about 1% to about 20% by weight, of dimethyl isosorbide
- from about 1% to about 40% by weight, preferably from about 5% to about 35% by weight of undecylenic acid
- from greater than 0 to about 30% by weight, preferably from greater than 0 to about 25% by weight, more preferably from about 0.5% to about 20% by weight, of the carboxylic acid component other than undecylenic acid
- from about 2% to about 55% by weight, preferably from about 5% to about 55% by weight, more preferably from about 10% to about 30% by weight, of the monohydric alcohol, and
- from 0 to about 25% by weight, preferably from about 1% to about 15% by weight, of the urea based component.

Although the preferred urea-based component is urea itself, a suitable urea-based component can comprise urea peroxide or carbamide peroxide. Urea-based components act as nail penetrators and/or softeners. Further, these urea-based components serve a cosmetic function in that they improve the visual appearance of the nail by hydrating and thinning hyperkeratotic nails, thereby providing an incentive for the user to be diligent in applying the DAC.

In addition to the urea-based component, the carrier of the present invention comprises a monohydric alcohol containing 2 to 4 carbon atoms. The monohydric alcohol can be ethanol, propanol, isopropanol, etc., isopropanol being preferred. Optionally, the carrier can contain up to about 7% water.

The carrier of the present invention also contains a carboxylic acid component other than undecylenic acid. Generally speaking, the carboxylic acid component comprises a C1 to C10 organic acid which can be alone and/or in an aqueous solution. Non-limiting examples of C1-C10 carboxylic acids suitable for use in the carrier of the present invention include saturated and/or unsaturated, linear and/or branched, aliphatic, mono-, di-, carboxylic acids, alkylaryl or aromatic dicarboxylic acids, oxy- and hydroxyl-carboxylic acids (e.g., alpha-hydroxy acids). Preferred carboxylic acids include formic acid, acetic acid, propionic acid, butyric acid, valeric acid, caproic acid, capyric acid, capric acid, sorbic acid, oxalic acid, hydroxybutyric acid, hydroxypropionic acids, lactic acid, glycolic acid, citric acid, malic acid, tartartic acid, malonic acid, fumaric acid, succinic acid, glutaric acid, apidic acid, pimelic acid, oxalacetic acid, phthalic acid, tartronic acid, pyruvic acid, and mixtures thereof. An especially preferred carboxylic acid is lactic acid.

One of the primary ingredients used in the carrier of the present invention is undecylenic acid (undec-10-enoic acid), an unsaturated fatty acid. While not wanting to be bound by any particular theory, it is believed undecylenic acid acts as a linking agent which brings certain components of the carrier together to enhance penetration. It is also believed that undecylenic acid can act as a biocide/antimicrobial to some extent and thereby enhance the stability of the carrier of the present invention. Further, when the carrier is used in forming a DAC employing an antifungal as the active ingredient, the undecylenic acid has the additional benefit that, in and of itself, in certain amounts it possesses antifungal properties thereby enhancing the efficacy of the DAC. Undecylenic acid also reduces the surface tension of and emulsifies other agents present in the carrier.

An important ingredient in the carrier of the present invention is dimethyl isosorbide (DMI).

A useful component which can be used in the carrier of the present invention can also include a diol containing from about 2 to about 4 carbon atoms. Non-limiting examples of suitable diols include ethylene glycol, propylene glycol, etc. A preferred diol is propylene glycol. If used, the diol will generally be present in an amount of from about 4 to about 15% by weight, preferably from about 4 to about 10% by weight.

Another useful component which can be used in the carrier comprises about 10% by weight of a carboxylic acid ester having the formula:

I

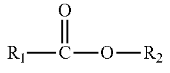

wherein $R_1$ comprises 1 to 3 carbon atoms, and $R_2$ comprises 2 to 4 carbon atoms.

Yet another useful component which may be used in the carrier comprises from about 2 to about 10% by weight of a fatty acid ester having the formula

II

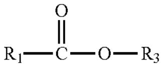

wherein $R_1$ comprises 1 to 3 carbon atoms, $R_3$ comprises 10 to 22 carbon atoms.

The adjunct components mentioned above, i.e., diols and esters, including the fatty acid esters, can be useful in certain applications to make the DACs more pleasing in smell and/or for ease in application. However, they are not considered to be critical components of the carrier and/or the DACs comprising the carrier.

A feature of the carrier of the present invention is that a wide variety of DAI's are dispersible in the carrier. In this regard the term "dispersible," "dispersion," or variants thereof is intended to mean and include a solution, an emulsion, a suspension, or a slurry to the extent the slurry can be formed into a uniform dispersion of particles/carrier with sufficient agitation and remain in that uniform state for a period of time sufficient for the carrier and its dispersed ingredient(s) to be uniformly applied to a skin surface, e.g., the nail and surrounding tissue.

As used herein "dermatologically active ingredient" (DAI) includes cosmetic and/or pharmaceutical components or compounds which, when applied to skin tissue, provide an aesthetic and/or curative effect. As noted, the carrier of the present invention is a liquid vehicle in which the DAI can be dissolved, suspended, dispersed, or emulsified. Thus, the DAC of the present invention, may form a single phase, e.g., a solution, or separate phases, e.g., a slurry, emulsion, suspension, or the like. In any event, when the constituents, e.g., the DAI forms a separate phase, as in a slurry, the slurry will be one which upon sufficient agitation can be formed into a uniform dispersion or suspension for a period of time to allow the DAC to be applied to the desired skin or nail area, the DAI being delivered to the affected skin area in a generally uniform fashion.

The DAC of the present invention may be prepared in a number of forms including creams, milks, solutions, tinctures, liniments, liquids, sprays, suspensions, gels, or lotions.

In respect of DAIs which are cosmetic in nature, it should be noted that the carrier composition of the present invention can be used to "bleach" and/or remove discoloration from nails which may have been caused by several well known underlying diseases. Thus, the DAC, from a cosmetic perspective, can be the carrier alone or have incorporated the DAIs such as skin softeners, emollients, etc.

With particular reference to the DAI comprising an antifungal, virtually any antifungal can be employed. For example, the following well known, widely used antifungals for skin tissue, including nails, includes, without limitation:

Azoles, including efinaconazole, clotrimazole, miconazole nitrate, ketoconazole, econazole, bifonazole, oxiconazole, tioconazole, sertaconazole, luliconazole, eberconazole, sulconazole, fenticonazole, fluconazole, preferably efinaconazole, clotrimazole, or miconazole nitrate.

Allylamines, including preferably, terbinafine, naftifine hydrochloride, butenafine hydrochloride, Morpholines, including preferably amorolfine hydrochloride Hydroxyquinolines, including preferably clioquinol Oxaboroles, including preferably tavaborole Thiocarbamates, including preferably tolfnaftate Iodines, including povidone iodine Pyridones, including preferably ciclopirox In a more preferred embodiment, the antifungal is selected from thiocarbamates, azoles, and allylamines, even more preferably tolnaftate, clotrimazole, and terbinafine, the most preferred antifungal being tolnaftate.

The above listed antifungals will be incorporated into the carrier forming one of the various types of dispersions noted above.

In general, when antifungals comprise the DAI, they will be present in an effective amount, wherein an effective amount means an amount necessary to affect a curative change in the fungus or other abnormality being treated. In this regard, it is well within the scope of the skilled artisan to determine what constitutes an effective amount. The literature is replete with compositions containing antifungals and the relative amounts used in such compositions. Accordingly, the skilled artisan would not have to engage in undue experimentation to determine what amount of antifungal should be used in the DACs of the present invention. As a general rule, when the antifungals comprise the DAI, they will comprise from greater than 0 to about 15% by weight or greater of the DAC.

To demonstrate the penetrating ability of the carrier composition and DACs made therefrom, a series of tests were performed as follows:

A) The antifungal component was mixed with dimethyl isosorbide, forming Mixture A.

B) Urea, undecylenic acid, lactic acid, and IPA were mixed together forming Mixture B.

C) Mixture A and Mixture B were combined.*

*The tolfnaftate sample was made in an earlier batch and was made as follows:

D) Tolnaftate was mixed with DMI and then undecylenic acid was added, forming Mixture D.

E) Urea, lactic acid and IPA were mixed together, forming Mixture E.

F) Mixture D and Mixture E were combined.

The compositions of the various DACs prepared are shown in Table 1.

TABLE 1

| Antifungal | Amount Antifungal (wt %) | DMI (wt %) | Urea (wt %) | Undecylenic Acid (wt %) | Lactic Acid (wt %) | IPA (wt %) | Form |
|---|---|---|---|---|---|---|---|
| Efinaconazle | 12.3 | 16 | 3.7 | 28.1 | 14.8 | 25.1 | Solution |
| Butenafine Hydrochloride | 1.4 | 18 | 4.2 | 31.5 | 16.6 | 28.3 | Solution |
| Amorolfine Hydrochloride | 6.6 | 17 | 3.9 | 29.9 | 15.8 | 26.8 | Solution |
| Clotrimazole | 1.4 | 18 | 4.2 | 31.5 | 16.6 | 28.3 | Solution |
| Clioquinol | 2.8 | 17.7 | 4.1 | 31.1 | 16.4 | 27.9 | Dispersible[1] |
| Terbinafine | 1.4 | 18 | 4.2 | 31.5 | 16.6 | 28.3 | Solution |
| Tolnaftate | 1.4 | 18 | 4.2 | 31.5 | 16.6 | 28.3 | Solution |
| Miconazole Nitrate | 2.8 | 17.7 | 4.1 | 31.1 | 16.4 | 27.9 | Dispersible[1] |
| Tavaborole | 6.6 | 17 | 3.9 | 29.9 | 15.8 | 26.8 | Solution |
| Naftifine Hydrochloride | 2.8 | 17.7 | 4.1 | 31.1 | 16.4 | 27.9 | Solution |
| Ciclopirox | 10.1 | 16.4 | 3.8 | 28.9 | 15.1 | 25.7 | Solution |

[1]Uniformly dispersible on shaking.

To demonstrate penetrating ability of the carrier and more specifically DACs prepared using the carrier of the present invention, the samples were tested against a commercial product sold under the name Jublia®. The antifungal in the Jublia® composition is efinaconazole and the vehicle is isopropanol as well as a surfactant and a volatile siloxane.

The penetration test was conducted using a substrate comprising polyurethane foam blocks marketed by Pacific Research Laboratories under the designation "Block 10 PCF" and commonly used for biomechanical testing. The faces of two blocks of the substrate were positioned between platens, the assembly of platens and substrate blocks being compressed together using the same and constant compression for each test. Each of the samples was dyed with fluorescein to improve visibility of the liquid. Two drops of each sample were applied at the top on the seam between the compressed substrate blocks. The samples were allowed to sit for 20 seconds, then the excess liquid was dabbed away. The samples were then allowed to dry for 2 minutes, after which the blocks were separated. The amount of penetration of the sample through the substrate was observed. As can be seen in FIG. 1, the borders of the penetration of the samples have been traced with a marker for ease of viewing. As can be seen, all of the compositions of the present invention penetrated further than the Jublia® composition.

As can be seen from the above results, the carrier compositions of the present invention are effective at dispersing, as that term is defined above, a wide variety of antifungals from varied classes of antifungals, all of which are known to have antifungal activity. Further, and importantly, when compared with the widely used Jublia® antifungal composition containing a lower alcohol such as isopropanol, the DACs of the present invention wherein the DAIs are antifungals show better penetrating ability than the Jublia® formulation. This is significant, as noted above, since in the Jublia® composition in order to enhance penetration, the compositions require, in addition to an alcohol, a surfactant, and a volatile silicone wetting agent. Importantly, unlike the Jublia® composition, the preferred embodiment of the present composition incorporates urea and lactic acid which collectively thin thickened nails, enhance nail hydration and diminish discoloration.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A pharmaceutically active composition for application to nails and surrounding tissue, comprising:

an effective amount of a pharmacologically active antifungal component; and a carrier, said carrier comprising:

from greater than 0 to about 40% by weight of dimethyl isosorbide;

from about 1 to about 40% by weight of undecylenic acid;

from greater than 0 to about 30% by weight of a carboxylic acid component other than undecylenic acid;

from about 2 to about 55% by weight of a monohydric alcohol having from 2 to 4 carbon atoms; and from greater than 0 to about 25% by weight of a urea based component, said antifungal component being uniformly dispersible in said carrier.

2. The composition of claim 1, wherein said composition comprises:

from greater than 0 to about 15% by weight of said antifungal component from about 1 to about 20% by weight of said dimethyl isosorbide;

from about 5 to about 35% by weight of said undecylenic acid;

from about 0.5 to about 20% by weight of said carboxylic acid component other than undecylenic acid;

from about 10 to about 30% by weight of said monohydric alcohol having from 2 to 4 carbon atoms; and from about 1 to about 15% by weight of said urea based component.

3. The composition of claim 1, further comprising from about 2 to about 10% by weight of a carboxylic acid ester having the formula:

I

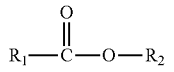

wherein $R_1$ comprises 1 to 3 carbon atoms, and $R_2$ comprises 2 to 4 carbon atoms.

4. The composition of claim 1, further comprising:

from about 2 to about 10% by weight of a fatty acid ester having the formula

II

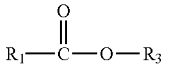

wherein $R_1$ comprises 1 to 3 carbon atoms, $R_3$ comprises 10 to 22 carbon atoms.

5. The composition of claim 1, wherein said urea-based component comprises urea.

6. The composition of claim 1, wherein said monohydric alcohol comprises isopropyl alcohol.

7. The composition of claim 1, wherein said carboxylic acid component is selected from the group consisting of formic acid, acetic acid, propionic acid, butyric acid, valeric acid, caproic acid, capyric acid, capric acid, sorbic acid, oxalic acid, hydroxybutyric acid, hydroxypropionic acids, lactic acid, glycolic acid, citric acid, malic acid, tartaric acid, malonic acid, fumaric acid, succinic acid, glutaric acid, apidic acid, pimelic acid, oxalacetic acid, phthalic acid, tartronic acid, pyruvic acid, and mixtures thereof.

8. The composition of claim 7, wherein said carboxylic acid comprises lactic acid.

9. The composition of claim 4, wherein said fatty acid ester comprises isopropyl myristate in an amount of from about 2 to about 10% by weight.

10. The composition of claim 1, further comprising from about 4 to about 10% by weight of a diol containing from 2 to 4 carbon atoms.

11. A carrier for use in topical application of dermatologically active ingredients, comprising:

from greater than 0 to about 40% by weight of dimethyl isosorbide;

from about 1 to about 40% by weight of undecylenic acid;

from greater than 0 to about 30% by weight of a carboxylic acid component other than undecylenic acid;

from about 2 to about 55% by weight of a monohydric alcohol having from 2 to 4 carbon atoms; and from greater than 0 to about 25% by weight of a urea based component.

12. The carrier of claim 11, comprising:

from about 1 to about 15% by weight of said dimethyl isosorbide;

from about 5 to about 25% by weight of said undecylenic acid;

from about 0.5 to about 10% by weight of said carboxylic acid component other than undecylenic acid;

from about 10 to about 30% by weight of said monohydric alcohol having from 2 to 4 carbon atoms; and from about 1 to about 15% by weight of said urea based component.

13. The composition of claim 11, further comprising from about 2 to about 10% by weight of a carboxylic acid ester having the formula:

I

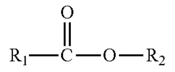

wherein $R_1$ comprises 1 to 3 carbon atoms, and $R_2$ comprises 2 to 4 carbon atoms.

14. The composition of claim 11, further comprising:

from about 2 to about 10% by weight of a fatty acid ester having the formula

II

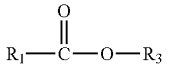

wherein $R_1$ comprises 1 to 3 carbon atoms, $R_3$ comprises 10 to 22 carbon atoms.

15. The composition of claim 11, wherein said urea-based component comprises urea.

16. The composition of claim 11, wherein said monohydric alcohol comprises isopropyl alcohol.

17. The composition of claim 11, wherein said carboxylic acid component is selected from the group consisting of formic acid, acetic acid, propionic acid, butyric acid, valeric acid, caproic acid, capyric acid, capric acid, sorbic acid, oxalic acid, hydroxybutyric acid, hydroxypropionic acids, lactic acid, glycolic acid, citric acid, malic acid, tartaric acid, malonic acid, fumaric acid, succinic acid, glutaric acid, apidic acid, pimelic acid, oxalacetic acid, phthalic acid, tartronic acid, pyruvic acid, and mixtures thereof.

18. The composition of claim 17, wherein said carboxylic acid comprises lactic acid.

19. The composition of claim 14, wherein said fatty acid ester comprises isopropyl myristate in an amount of from about 2 to about 10% by weight.

20. The composition of claim 11, further comprising from about 4 to about 10% by weight of a diol containing from 2 to 4 carbon atoms.

* * * * *